(12) United States Patent  
Miyazaki (10) Patent No.: US 10,357,152 B2  
(45) Date of Patent: Jul. 23, 2019

(54) GLASSES-SHAPED ELECTRONIC DEVICE

(71) Applicant: Alps Alpine Co., Ltd., Ota-ku, Tokyo (JP)

(72) Inventor: Shun Miyazaki, Miyagi-ken (JP)

(73) Assignee: Alps Alpine Co., Ltd., Tokyo (JP)

( * ) Notice: Subject to any disclaimer, the term of this patent is extended or adjusted under 35 U.S.C. 154(b) by 0 days.

(21) Appl. No.: 15/801,221

(22) Filed: Nov. 1, 2017

(65) Prior Publication Data

US 2018/0070812 A1 Mar. 15, 2018

Related U.S. Application Data

(63) Continuation of application No. PCT/JP2016/065821, filed on May 27, 2016.

(30) Foreign Application Priority Data

Jun. 1, 2015 (JP) .................................. 2015-111665

(51) Int. Cl.
*A61B 3/10* (2006.01)
*A61B 5/0496* (2006.01)
(Continued)

(52) U.S. Cl.
CPC .............. *A61B 3/10* (2013.01); *A61B 5/0496* (2013.01); *A61B 5/6803* (2013.01);
(Continued)

(58) Field of Classification Search
CPC ... A61B 5/0496; A61B 5/6844; A61B 5/6803; A61B 3/113; A61B 3/10; A61B 5/0478;
(Continued)

(56) References Cited

U.S. PATENT DOCUMENTS 5,606,743 A * 2/1997 Vogt ..................... H04B 1/086  
                                                                      16/228
6,769,767 B2 * 8/2004 Swab ................ H04W 56/0015  
                                                                      351/158

(Continued)

FOREIGN PATENT DOCUMENTS

EP        2668898      12/2013  
JP     2002-297088    10/2002  
(Continued)

OTHER PUBLICATIONS

European Search Report from European Application No. 16803284 dated Nov. 15, 2018.
International Search Report from International Application No. PCT/JP2016/065821 dated Aug. 2, 2016.

*Primary Examiner* — William R Alexander  
*Assistant Examiner* — Henry A Duong  
(74) *Attorney, Agent, or Firm* — Beyer Law Group LLP (57) ABSTRACT

A left electronic-component compartment has a left FPC receiving port, through which a flexible printed circuit (FPC) is inserted into the left electronic-component compartment, located adjacent to a left hinge. In the left electronic-component compartment, a left waterproof member is fitted adjacent to a left connector, which serves as a connection between the FPC and a battery. The left waterproof member prevents moisture, dust, and other foreign matter from entering the battery. A right electronic-component compartment has a right FPC receiving port, through which the FPC is inserted into the right electronic-component compartment, located adjacent to a right hinge. In the right electronic-component compartment, a right waterproof member is fitted adjacent to a right connector, serving as a connection between the FPC and electric circuitry. The right waterproof member prevents moisture, dust, and other foreign matter from entering the electric circuitry.

8 Claims, 6 Drawing Sheets

(51) Int. Cl.
 *G02C 11/00* (2006.01)
 *A61B 5/00* (2006.01)
(52) U.S. Cl.
 CPC ............ *A61B 5/6819* (2013.01); *G02C 11/00* (2013.01); *A61B 2560/0425* (2013.01); *A61B 2560/0468* (2013.01); *A61B 2562/0219* (2013.01); *A61B 2562/18* (2013.01); *A61B 2562/222* (2013.01); *G02C 11/10* (2013.01)
(58) Field of Classification Search
 CPC ..... A61B 5/0408; A61B 3/102; A61B 3/1025; A61B 3/103; A61B 5/6819; A61B 2562/222; A61B 2562/18; A61B 2560/0468; A61B 2560/0425; A61B 2562/0219; G02C 11/10; G02C 5/22; G02C 5/14; G02C 5/02; G02C 11/00
 USPC ........................................................ 351/205
 See application file for complete search history.

(56) References Cited

U.S. PATENT DOCUMENTS

| 9,107,622 | B2 | 8/2015 | Nistico et al. | |
|---|---|---|---|---|
| 9,433,369 | B2* | 9/2016 | Kanoh | .................... A61B 3/10 |
| 2013/0250233 | A1* | 9/2013 | Blum | .................... G02C 11/10 |
| | | | | 351/158 |
| 2015/0042544 | A1 | 2/2015 | Sugihara et al. | |
| 2015/0131048 | A1 | 5/2015 | Iurilli | |

FOREIGN PATENT DOCUMENTS

| JP | 2012-85747 | 5/2012 |
|---|---|---|
| JP | 2013-244370 | 12/2013 |
| JP | 2014-512596 | 5/2014 |

\* cited by examiner

GLASSES-SHAPED ELECTRONIC DEVICE

CLAIM OF PRIORITY

This application is a Continuation of International Application No. PCT/JP2016/065821 filed on May 27, 2016, which claims benefit of Japanese Patent Application No. 2015-111665 filed on Jun. 1, 2015. The entire contents of each application noted above are hereby incorporated by reference.

BACKGROUND OF THE INVENTION

1. Field of the Invention

The present invention relates to a glasses-shaped electronic device to be mounted on the head of a human to detect characteristics of the human.

2. Description of the Related Art

Electrodermal activity has been known as parameters indicating human psychological activity and physical conditions. For the electrodermal activity of a human, the potentials of the skin of the human are detected, so that the characteristics of the human can be detected.

Glasses-shaped electronic devices are currently required to detect the potentials of the skin of a human, particularly, the potentials (eye potentials) of the surface of the nose so that a variety of biological information about the human can be obtained based on the potentials. Examples of these devices include a device disclosed in Japanese Unexamined Patent Application Publication No. 2013-244370.

This device includes a pair of electrodes for detecting eye potentials such that the electrodes are arranged on the surfaces of nose pads of an eyeglass frame. The device further includes an electrode for detecting an eye potential such that the electrode is disposed on the surface of a bridge of the eyeglass frame. The eye potentials detected by the electrodes are transmitted as electrooculogram signals to an external electrooculogram processing unit connected to the electrodes by electric wiring lines, serving as conductors. The processing unit processes the signals.

As regards how to route the electric wiring lines, the electric wiring lines can be arranged on the outside of the eyeglass frame. If the electric wiring lines are exposed on the outside of the eyeglass frame, a user may touch the electric wiring lines with, for example, his or her finger, when using the device. The electric wiring lines may be broken.

Although the electric wiring lines can be received in the eyeglass frame, moisture, dust, or other foreign matter may enter an electric-wiring-line compartment provided in the eyeglass frame through, for example, an electric-wiring-line receiving port, and further enter, for example, an electronic component received in the eyeglass frame.

Furthermore, a space in the electric-wiring-line compartment in the eyeglass frame is limited because the eyeglass frame is thin. It is therefore difficult in view of structure to arrange the electric wiring lines in the eyeglass frame. A wiring operation is also complicated.

When the electric wiring lines are arranged inside the eyeglass frame, it is necessary to maintain stable connection between the electric wiring lines and, for example, an electronic component received in the eyeglass frame.

SUMMARY OF THE INVENTION

The present invention has been made in view of the above-described circumstances and provides a glasses-shaped electronic device capable of preventing moisture, dust, and other foreign matter from entering an electronic circuit component received in an eyeglass frame and a human characteristic detecting unit mounted in the eyeglass frame and capable of maintaining stable connection between the electronic circuit component and a conductor.

An aspect of the present invention provides a glasses-shaped electronic device including an eyeglass frame that includes a bridge, rims, hinges, temples, and temple tips and that has a first conductor compartment extending through each of the temples and the corresponding one of the temple tips and a second conductor compartment extending through the rims and the bridge, an electronic circuit component received in at least one of the temple tips of the eyeglass frame, a human characteristic detecting unit mounted in the bridge of the eyeglass frame and configured to detect an eye potential while being in contact with a human nose, and a conductor received in the first conductor compartments and the second conductor compartment such that the conductor extends through the first conductor compartments, the hinges, and the second conductor compartment. The conductor establishes electrical connection between the electronic circuit component and the human characteristic detecting unit. The device further includes a first waterproof member preventing moisture, dust, and other foreign matter from entering the electronic circuit component. The first waterproof member is fitted in the first conductor compartment. The device further includes a second waterproof member preventing moisture, dust, and other foreign matter from entering the human characteristic detecting unit. The second waterproof member is fitted in the second conductor compartment.

The above-described configuration can prevent moisture, dust, and other foreign matter from entering the electronic circuit component received in the temple tip of the eyeglass frame and the human characteristic detecting unit mounted in the eyeglass frame.

In one aspect, the first waterproof member may be fitted adjacent to a connection between the conductor and the electronic circuit component in the first conductor compartment and the second waterproof member may be fitted adjacent to a connection between the conductor and the human characteristic detecting unit in the second conductor compartment. Such a configuration can further enhance a waterproof function of preventing moisture, dust, and other foreign matter from entering the electronic circuit component and the human characteristic detecting unit.

In one aspect, the conductor may include a flexible printed circuit. Such a configuration facilitates conductor wiring in the eyeglass frame.

In one aspect, the flexible printed circuit may be connected at a first end to the electronic circuit component by a connector. Such a configuration facilitates connection between the flexible printed circuit and the electronic circuit component.

In one aspect, the glasses-shaped electronic device may further include a positioning retainer disposed in the first conductor compartment. The first end of the flexible printed circuit may be attached to the connector by the positioning retainer. Such a configuration can maintain stable connection between the conductor and the electronic circuit component.

DESCRIPTION OF THE PREFERRED EMBODIMENTS

Figure 1:
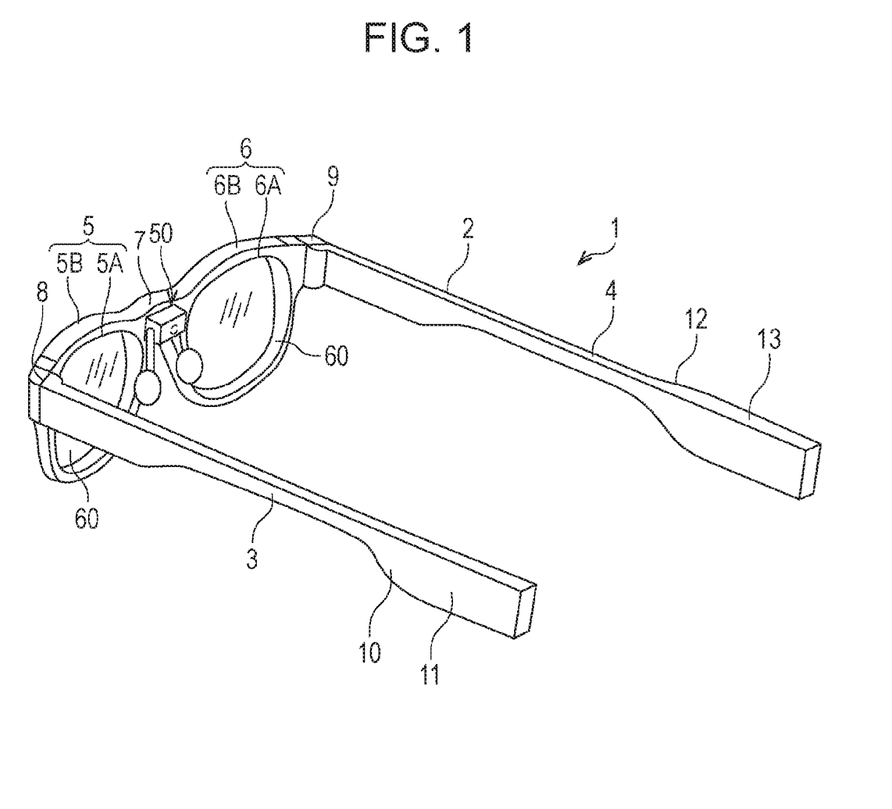
FIG. 1 is a rear perspective view of a glasses-shaped electronic device according to an embodiment of the present invention.

A glasses-shaped electronic device 1 according to an embodiment of the present invention will be described below with reference to the drawings. As illustrated in FIG. 1, the glasses-shaped electronic device 1 includes an eyeglass frame 2 made of plastic.

The eyeglass frame 2 includes a left temple 3 to be put on the left ear of a human and a right temple 4 to be put on the right ear of the human. These temples 3 and 4, each of which is not angled for fitting on the ear, have a linear shape to hold right and left temporal portions of the head of the human. The eyeglass frame 2 including the temples 3 and 4 having such a shape provides a comfortable tight fit.

The eyeglass frame 2 further includes a left rim 5 and a right rim 6 to which lenses 60 are secured. The rims 5 and 6 are coupled by a bridge 7. A human characteristic detecting unit 50, which will be described later, for detecting an eye potential is mounted in the bridge 7 such that the unit 50 can be placed on the nose of a human. The present invention can also be applied to a device that eliminates the human characteristic detecting unit 50.

In addition, a left hinge 8 is disposed between the left temple 3 and the left rim 5 and a right hinge 9 is disposed between the right temple 4 and the right rim 6. The temples 3 and 4 are connected to the rims 5 and 6 by the hinges 8 and 9, respectively, such that the temples are pivotable, or movable relative to the rims. When the glasses-shaped electronic device 1 is not used, typically, the left temple 3 of the eyeglass frame 2 is moved inwardly and the right temple 4 is then moved inwardly so as to be superposed on the left temple 3.

The left temple 3 is integrally formed with a left sloping portion 10 and a left temple tip 11, which serve as an end portion to be put on the left ear, such that the left sloping portion 10 is interposed between the left temple 3 and the left temple tip 11. The right temple 4 is integrally formed with a right sloping portion 12 and a right temple tip 13, which serve as an end portion to be put on the right ear, such that the right sloping portion 12 is interposed between the right temple 4 and the right temple tip 13. These temple tips 11 and 13 are typically called eyeglass tips, ear retainers, or ear pads. Part connecting the temple 3 and the temple tip 11 and part connecting the temple 4 and the temple tip 13 are portions on which the weight of the glasses-shaped electronic device 1 acts.

Figure 2:
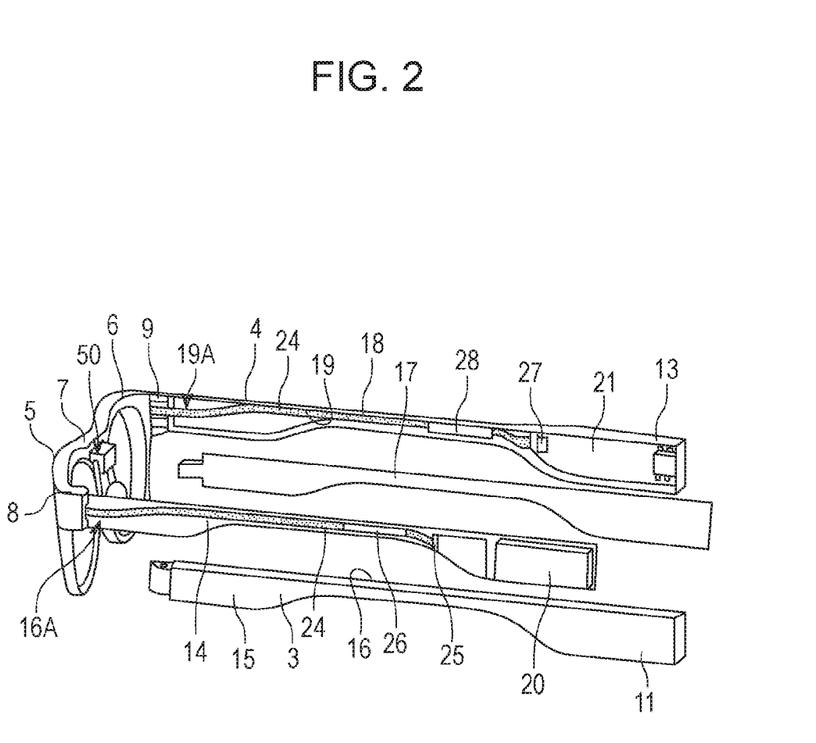
FIG. 2 is an explode perspective view illustrating a left temple and a right temple of the glasses-shaped electronic device.

As illustrated in FIG. 2, the left temple 3 and the left temple tip 11 can be divided into two portions, or an inner half portion 14 and an outer half portion 15. The half portions 14 and 15 are superposed on each other to define therebetween an elongated left electronic-component compartment 16, serving as a first conductor compartment, extending through the left temple 3 and the left temple tip 11.

Furthermore, the right temple 4 and the right temple tip 13 can also be divided into two portions, or an inner half portion 17 and an outer half portion 18. The half portions 17 and 18 are superposed on each other to define therebetween an elongated right electronic-component compartment 19, serving as a first conductor compartment, extending through the right temple 4 and the right temple tip 13.

The sloping portions 10 and 12 allow the temple tips 11 and 13 to be thicker than the temples 3 and 4, respectively. Such a configuration provides larger storage spaces in the temple tips 11 and 13 than those in the temples 3 and 4.

The left electronic-component compartment 16 accommodates a rectangular battery 20, serving as an electronic circuit component, in the left temple tip 11. The battery 20 is mounted in the whole of the storage space, located in the left temple tip 11, in the left electronic-component compartment 16. The inside of the left temple tip 11 serves as a dedicated mounting space for the battery 20. Thus, a large capacity battery can be received.

The right electronic-component compartment 19 accommodates electric circuitry 21, serving as an electronic circuit component, in the right temple tip 13. The electric circuitry 21 includes a charging circuit 22 for the battery 20. A power switch unit (not illustrated) is disposed in the right temple tip 13.

The electric circuitry 21 includes electronic components, such as a sensor unit 23 for detecting the posture of a human. The sensor unit 23 includes an acceleration sensor and a gyroscopic sensor. The acceleration sensor is a sensor that detects acceleration acting on the glasses-shaped electronic device 1. The acceleration sensor detects angular velocities in a plurality of axial directions (e.g., two or three axes) orthogonal to each other or one another. The gyroscopic sensor is a sensor that detects rotations acting on the glasses-shaped electronic device 1. The sensor unit in the present invention may include a six-axis gyroscopic sensor or a barometric pressure sensor. The sensor unit may include any kind of sensor.

The sensor unit 23 detects a performance characteristic of a user, for example, the posture, motion, or vibration of the user. A signal indicating the performance characteristic detected by the sensor unit 23 is transmitted to a portable communication terminal, such as a smartphone, by wireless communication, such as Bluetooth® or a wireless local area network (LAN).

Figure 3:
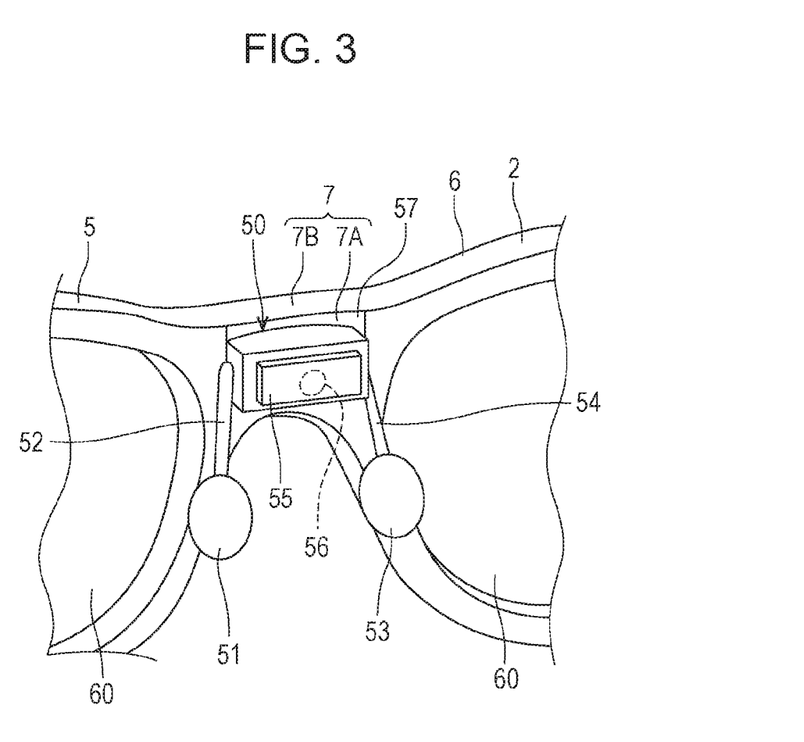
FIG. 3 is an enlarged rear perspective view illustrating part including a human characteristic detecting unit of the glasses-shaped electronic device.

As illustrated in FIG. 3, the human characteristic detecting unit 50 is mounted in the bridge 7 of the eyeglass frame 2. The human characteristic detecting unit 50 detects the potential (e.g., eye potential) of the surface of the nose of a human. The detection can be used to obtain a variety of information, for example, information on fatigue of human eyes, based on the temperature of the skin.

The human characteristic detecting unit 50 includes a left nose electrode pad 51 that is to be located on a first side of the bridge of the nose of a human and is to contact the surface of the nose, a rod-shaped left nose electrode member 52 having an end to which the left nose electrode pad 51 is secured, a right nose electrode pad 53 that is to be located on a second side of the bridge of the nose of the human and is to contact the surface of the nose, and a rod-shaped right nose electrode member 54 having an end to which the right nose electrode pad 53 is secured.

The human characteristic detecting unit 50 further includes a plate-shaped glabella electrode pad 55 to contact the surface of part above the nose and between the eyebrows of a human and a rod-shaped glabella electrode member 56 having an end secured to central part of a rear surface of the glabella electrode pad 55.

The left nose electrode member 52, the right nose electrode member 54, and the glabella electrode member 56 are electrically connected to a printed wiring board 58 disposed in the human characteristic detecting unit 50. The left nose electrode member 52 detects the eye potential of the left eye, the right nose electrode member 54 detects the eye potential of the right eye, and the glabella electrode member 56 detects an eye potential.

Examples of a material for the left nose electrode member 52, the right nose electrode member 54, and the glabella electrode member 56 include copper, titanium, and stainless steel. The nose electrode members 52 and 54 and the glabella electrode member 56 may be made of a conductive material. For a material for the nose electrode pads 51 and 53 and the glabella electrode pad 55, each pad may be made of copper, titanium, or stainless steel. Each pad may be plated with, for example, copper or titanium.

The electronic-component compartments 16 and 19 accommodate a single flexible printed circuit (hereinafter, referred to as an FPC) 24, serving as a conductor. The FPC 24 establishes electrical connection between the battery 20, the electric circuitry 21, and the printed wiring board 58 in the human characteristic detecting unit 50.

The use of the FPC 24 as conductor wiring lines in the glasses-shaped electronic device 1 facilitates wiring in the eyeglass frame 2 having narrow, limited storage spaces therein. In addition, since wiring lines of the FPC 24 are not exposed on the outside of the glasses-shaped electronic device 1, the glasses-shaped electronic device with excellent design quality can be provided.

The left electronic-component compartment 16 is defined between the two portions, or the inner half portion 14 and the outer half portion 15. The right electronic-component compartment 19 is also defined between the two portions, the inner half portion 17 and the outer half portion 18. To mount the FPC 24 in the electronic-component compartments 16 and 19, the inner and outer half portions 14 and 15 can be separated from each other and the inner and outer half portions 17 and 18 can be separated from each other. This leads to increased workability of mounting the FPC 24.

Figure 4:
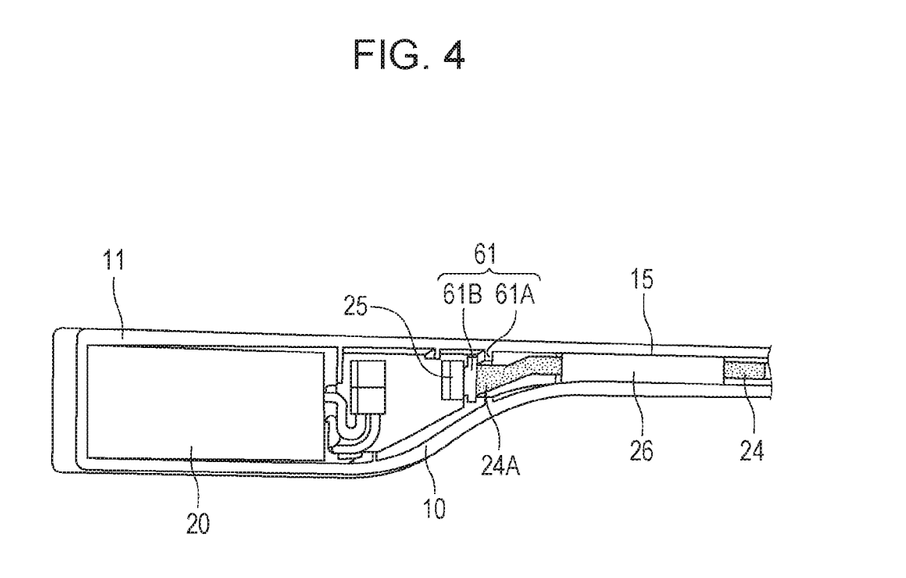
FIG. 4 is an exploded, enlarged perspective view of part including a left temple tip of the glasses-shaped electronic device.

As illustrated in FIG. 4, the left electronic-component compartment 16 accommodates a left connector 25 in the left sloping portion 10. Preferably, the battery 20 is connected to a left end 24A of the FPC 24 by the left connector 25.

Preferably, a left FPC positioning retainer 61 is disposed in the vicinity of the left connector 25 in the left electronic-component compartment 16. The left FPC positioning retainer 61 includes a rib 61A disposed in the outer half portion 15 and a flange 61B attached to the left end 24A of the FPC 24.

Engagement of the flange 61B with the rib 61A prevents the left end 24A of the FPC 24 from detaching from the left connector 25. Thus, stable connection between the FPC 24 and the battery 20 can be maintained under tension on the FPC 24 when the FPC 24 is mounted in the left electronic-component compartment 16 or the left temple 3 is moved inwardly.

The left electronic-component compartment 16 has a left FPC receiving port 16A, through which the FPC 24 is inserted into the left electronic-component compartment 16, located adjacent to the left hinge 8.

In the left electronic-component compartment 16, preferably, a left waterproof member 26, serving as a first waterproof member, is fitted adjacent to the left connector 25, which serves as a connection between the FPC 24 and the battery 20. The left waterproof member 26 prevents moisture, dust, and other foreign matter from entering the battery 20 and is made of, for example, PORON®.

If moisture, dust, or other foreign matter enters the left electronic-component compartment 16 through the left FPC receiving port 16A, the moisture, dust, or other foreign matter would deposit on an inner wall of the elongated left electronic-component compartment 16 and would accordingly fail to reach the battery 20. If moisture, dust, or other foreign matter approaches the left connector 25, the left waterproof member 26 can eventually prevent the moisture, dust, or other foreign matter from entering the battery 20.

In the present invention, the fitting position of the left waterproof member 26 in the left electronic-component compartment 16 is not limited to the vicinity of the connection between the FPC 24 and the battery 20, provided that the left waterproof member 26 can prevent moisture, dust, and other foreign matter from entering the battery 20. The left waterproof member 26 can be fitted at any of various positions in the left electronic-component compartment 16.

Figure 5:
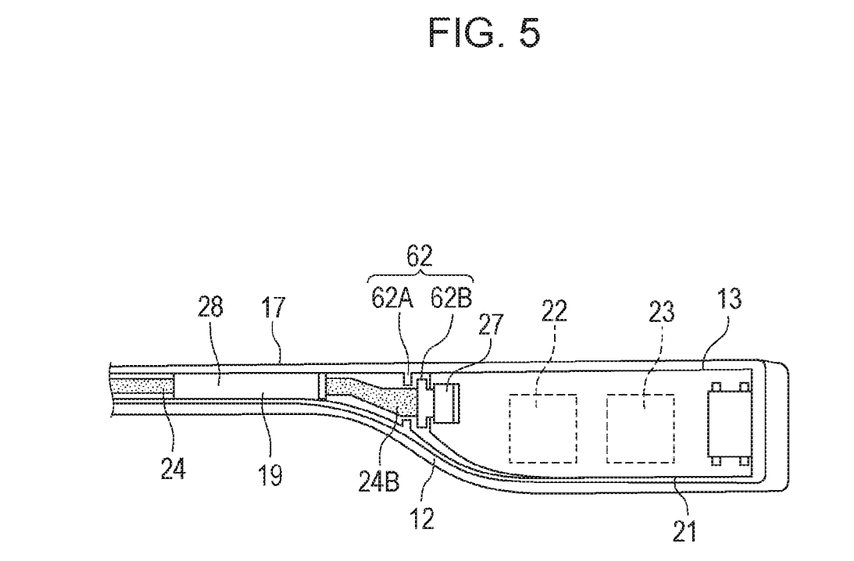
FIG. 5 is an exploded, enlarged perspective view of part including a right temple tip of the glasses-shaped electronic device.

As illustrated in FIG. 5, the right electronic-component compartment 19 accommodates a right connector 27 in the right sloping portion 12. Preferably, the electric circuitry 21 is connected to a right end 24B of the FPC 24 by the right connector 27.

Preferably, a right FPC positioning retainer 62 is disposed in the vicinity of the right connector 27 in the right electronic-component compartment 19. The right FPC positioning retainer 62 includes a rib 62A disposed in the outer half portion 17 and a flange 62B attached to the right end 24B of the FPC 24.

Engagement of the flange 62B with the rib 62A prevents the right end 24B of the FPC 24 from detaching from the right connector 27. Thus, stable connection between the FPC 24 and the electric circuitry 21 can be maintained under tension on the FPC 24 when the FPC 24 is mounted in the right electronic-component compartment 19 or the right temple 4 is moved inwardly.

The right electronic-component compartment 19 has a right FPC receiving port 19A, through which the FPC 24 is inserted into the right electronic-component compartment 19, located adjacent to the right hinge 9. In the right electronic-component compartment 19, preferably, a right waterproof member 28, serving as a first waterproof member, is fitted adjacent to the right connector 27, which serves as a connection between the FPC 24 and the electric circuitry 21. The right waterproof member 28 prevents moisture, dust, and other foreign matter from entering the electric circuitry 21 and is made of, for example, PORON®.

If moisture, dust, or other foreign matter enters the right electronic-component compartment 19 through the right FPC receiving port 19A, the moisture, dust, or other foreign matter would deposit on an inner wall of the elongated right electronic-component compartment 19 and would accordingly fail to reach the electric circuitry 21. If moisture, dust, or other foreign matter approaches the right connector 27, the right waterproof member 28 can eventually prevent the moisture, dust, or other foreign matter from entering the electric circuitry 21.

In the present invention, the fitting position of the right waterproof member 28 in the right electronic-component compartment 19 is not limited to the vicinity of the connection between the FPC 24 and the electric circuitry 21, provided that the right waterproof member 28 can prevent moisture, dust, and other foreign matter from entering the electric circuitry 21. The right waterproof member 28 can be fitted at any of various positions in the right electronic-component compartment 19.

In the present invention, the FPC 24 may, instead of being a single piece, include a plurality of pieces coupled to each other or one another. The FPC has only to have a function of establishing electrical connection between the battery 20, the electric circuitry 21, and the printed wiring board 58 in the human characteristic detecting unit 50.

Figure 6:
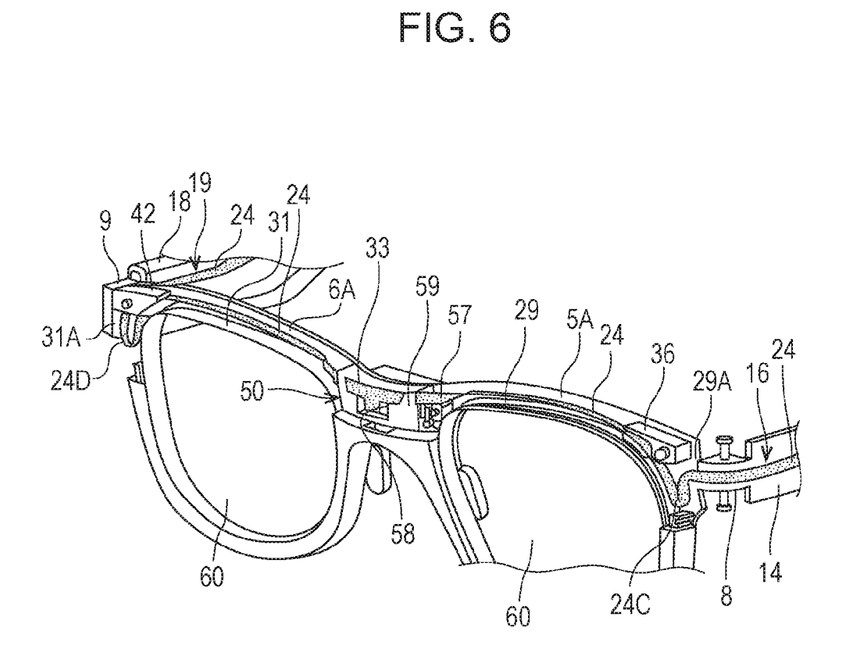
FIG. 6 is an exploded, enlarged perspective view of the glasses-shaped electronic device and illustrates a mounted state of a flexible printed circuit in the glasses-shaped electronic device.

Upper part of the left rim 5 of the eyeglass frame 2 can be divided into two portions, or an inner half portion 5A and an outer half portion 5B. An FPC compartment 29, which is included in a second conductor compartment, is defined between the half portions 5A and 5B. The left part of the FPC 24 is received such that the left part extends through the FPC compartment 29 in the left rim 5, the left hinge 8, and the left electronic-component compartment 16.

Upper part of the right rim 6 of the eyeglass frame 2 can also be divided into two portions, or an inner half portion 6A and an outer half portion 6B. An FPC compartment 31, which is included in the second conductor compartment, is defined between the half portions 6A and 6B. The right part of the FPC 24 is received such that the right part extends through the FPC compartment 31 in the right rim 6, the right hinge 9, and the right electronic-component compartment 19.

The bridge 7 can also be divided into two portions, or an inner half portion 7A and an outer half portion 7B. An FPC compartment 33 is defined between the half portions 7A and 7B. This, the left part and the right part of the FPC 24 join in the FPC compartment 33 in the bridge 7.

As illustrated in FIG. 6, the FPC compartment 29 in the left rim 5 is curved and slit-shaped. In the FPC compartment 29, the FPC 24 is held such that a main surface of the FPC 24 extends substantially horizontally. Thus, the FPC 24 can be received in a narrow portion of glasses, such as a rim thereof.

The FPC 24 held in the FPC compartment 29 has a left deformable bend 24C. Part of the FPC 24 extending from the left deformable bend 24C to the left hinge 8 is twisted by substantially 90° at an entrance to the left hinge 8. The FPC 24 is received in the left electronic-component compartment 16. The FPC 24 is held in the left electronic-component compartment 16 such that the main surface of the FPC 24 extends substantially vertically.

The FPC 24 does not experience tension when the left temple 3 is moved inwardly. Thus, there is no possibility of a break in the FPC 24. The stable connection between the FPC 24 and the battery 20 can be maintained.

A left FPC positioning member 36 for preventing the FPC 24 from floating in the FPC compartment 29 is secured to the FPC compartment 29 in the left rim 5 such that the left FPC positioning member 36 is pressed against the outer half portion 5B of the left rim 5.

The left FPC positioning member 36 supports the FPC 24 in the FPC compartment 29 such that the main surface of the FPC 24 can extend substantially horizontally if the FPC 24 is twisted, thus maintaining stable mounting of the FPC 24.

When the FPC 24 is mounted in the left rim 5, the FPC 24 can be temporarily fixed in the FPC compartment 29 by the left FPC positioning member 36. The left rim 5 can be assembled without interference with the FPC 24.

The FPC compartment 31 in the right rim 6 is curved and slit-shaped. In the FPC compartment 31, the FPC 24 is held such that the main surface of the FPC 24 extends substantially horizontally. Thus, the FPC 24 can be received in a narrow portion of glasses, such as a rim thereof.

The FPC 24 held in the FPC compartment 31 has a right deformable bend 24D. Part of the FPC 24 extending from the right deformable bend 24D to the right hinge 9 is twisted by substantially 90° at an entrance to the right hinge 9. The FPC 24 is received in the right electronic-component compartment 19. The FPC 24 is held in the right electronic-component compartment 19 such that the main surface of the FPC 24 extends substantially vertically.

The FPC 24 does not experience tension when the right temple 4 is moved inwardly. Thus, there is no possibility of a break in the FPC 24. The stable connection between the FPC 24 and the electric circuitry 21 can be maintained.

A right FPC positioning member 42 for preventing the FPC 24 from floating in the FPC compartment 31 is secured to the FPC compartment 31 in the right rim 6 such that the right FPC positioning member 42 is pressed against the outer half portion 6B of the right rim 6.

The right FPC positioning member 42 supports the FPC 24 in the FPC compartment 31 such that the main surface of the FPC 24 can extend substantially horizontally if the FPC 24 is twisted, thus maintaining stable mounting of the FPC 24.

When the FPC 24 is mounted in the right rim 6, the FPC 24 can be temporarily fixed in the FPC compartment 31 by the right FPC positioning member 42. The right rim 6 can be assembled without interference with the FPC 24.

Parts of the FPC 24 received in the FPC compartments 29 and 31 and located adjacent to the bridge 7 are twisted such that the main surface of the FPC 24 is turned by substantially 90°. The FPC 24 is caught by a central waterproof member 59, which serves as a second waterproof member and is disposed in the human characteristic detecting unit 50 and is made of PORON (registered trademark), for example. The FPC 24 is attached to and pressed against an inner wall surface of the outer half portion 7B of the bridge 7 by a casing 57 of the human characteristic detecting unit 50 such that the main surface of the FPC 24 extends substantially vertically. Consequently, the FPC 24 is prevented from floating in the bridge 7, thus maintaining stable holding of the FPC 24.

The FPC 24 in the human characteristic detecting unit 50 is electrically connected to the printed wiring board 58 such that a detection signal can be transmitted to the electric circuitry 21.

The FPC compartment 29 has an FPC receiving port 29A, through which the FPC 24 is inserted into the FPC compartment 29, located adjacent to the left hinge 8. In the FPC compartment 29, the central waterproof member 59 is fitted adjacent to a connection between the FPC 24 and the printed wiring board 58.

If moisture, dust, or other foreign matter enters the FPC compartment 29 through the FPC receiving port 29A, the moisture, dust, or other foreign matter would deposit on an inner wall of the slit-shaped, elongated FPC compartment 29 and would accordingly fail to reach the printed wiring board 58. If moisture, dust, or other foreign matter approaches the central waterproof member 59, the central waterproof member 59 can eventually prevent the moisture, dust, or other foreign matter from entering the printed wiring board 58.

In the present invention, the waterproof member may be fitted at any position in the FPC compartment 29, provided that the waterproof member can prevent moisture, dust, and other foreign matter from entering the human characteristic detecting unit 50. The waterproof member can be fitted at any of various positions in the FPC compartment 29.

The FPC compartment 31 has an FPC receiving port 31A, through which the FPC 24 is inserted into the FPC compartment 31, located adjacent to the right hinge 9. In the FPC compartment 31, the central waterproof member 59 is fitted adjacent to a connection between the FPC 24 and the printed wiring board 58.

If moisture, dust, or other foreign matter enters the FPC compartment 31 through the FPC receiving port 31A, the moisture, dust, or other foreign matter would deposit on an inner wall of the slit-shaped, elongated FPC compartment 31 and would accordingly fail to reach the printed wiring board 58. If moisture, dust, or other foreign matter approaches the central waterproof member 59, the central waterproof member 59 can eventually prevent the moisture, dust, or other foreign matter from entering the printed wiring board 58.

In the present invention, the waterproof member may be fitted at any position in the FPC compartment 31, provided that the waterproof member can prevent moisture, dust, and other foreign matter from entering the human characteristic detecting unit 50. The waterproof member can be fitted at any of various positions in the FPC compartment 31.

In the above-described glasses-shaped electronic device 1, if moisture, dust, or other foreign matter enters the compartments 16, 19, 29, and 31 through the FPC receiving ports 16A, 19A, 29A, and 31A in the eyeglass frame 2, the waterproof members 26, 28, and 59 can prevent the moisture, dust, or other foreign matter from entering the battery 20, the electric circuitry 21, and the human characteristic detecting unit 50.

The FPC positioning retainers 61 and 62 prevent the respective ends 24A and 24B of the FPC 24 from detaching from the connectors 25 and 27. Thus, the stable connection between the FPC 24, the battery 20, and the electric circuitry 21 can be maintained.

The above-described embodiment is not intended to limit the present invention. It should be understood by those skilled in the art that various modifications, combinations, and alternations of the components of the above-described embodiment may be made within the technical scope of the present invention or the equivalents thereof.

The glasses-shaped electronic device according to the present invention is also used as a device to be mounted on the head of a human to detect the posture of the human, and can be used to collect data in order to, for example, prevent a driver of a car from dozing or increase the running speed of an athlete.

What is claimed is:

1. A glasses-shaped electronic device comprising:
an eyeglass frame having a bridge, a pair of rims, a pair of hinges, a pair of temples, and a pair of temple tips, the eyeglass frame further including:
  a pair of first conductor compartments each formed within and extending through corresponding one of the temples and the corresponding one of the temple tips; and
  a second conductor compartment formed within and extending from the bridge on both sides through the rims;
  an electronic circuit component received in at least one of the first conductor compartments at the corresponding one of the temple tips;
  a human characteristic detecting unit mounted in the bridge, the human characteristic detecting unit detecting an eye potential while being in contact with a human nose;
  a conductor received in the first conductor compartments and the second conductor compartment such that the conductor extends from the bridge to both sides thereof through the second conductor compartment, the hinges, and the first conductor compartments so as to establish electrical connection between the human characteristic detecting unit and the electronic circuit component,
wherein each of the first conductor compartments includes a first opening to receive the conductor therethrough into the first conductor compartment, the eyeglass frame further comprising:
  at least one first waterproof member fitted in at least one of the first conductor compartments and disposed between the first opening and the electronic circuit component, thereby preventing moisture, dust, or foreign matter, which entered the first conductor compartment through the first opening, from entering the electronic circuit component.

2. The electronic device according to claim 1, wherein the conductor includes a flexible printed circuit.

3. The electronic device according to claim 2, wherein a first end of the flexible printed circuit is connected to the electronic circuit component by a connector.

4. The electronic device according to claim 3, wherein the first end of the flexible printed circuit is attached to the connector by a positioning retainer disposed in the corresponding one of the first conductor compartment.

5. The electronic device according to claim 1, wherein the second conductor compartment includes at least one second openings to receive the conductor therethrough into the second conductor compartment, the eyeglass frame further comprising:
  a second waterproof member fitted in the second conductor compartment and disposed between the at least one second opening and the human characteristic detecting unit, thereby preventing moisture, dust, or foreign matter, which entered the second conductor compartment through the at least one second opening, from entering the human characteristic detecting unit.

6. The electronic device according to claim 5, wherein the first waterproof member is fitted near a connection between the conductor and the electronic circuit component in the first conductor compartment, and the second waterproof member is fitted near a connection between the conductor and the human characteristic detecting unit in the second conductor compartment.

7. The electronic device according to claim 5, wherein the second opening is formed on the rim near corresponding one of the hinges.

8. The electronic device according to claim 1, wherein the first opening is formed on the temple near corresponding one of the hinges.

* * * * *